United States Patent
Lacombe et al.

(10) Patent No.: US 7,572,946 B2
(45) Date of Patent: Aug. 11, 2009

(54) PROCESS FOR OLIGOMERIZING OLEFINS USING A SILICA-ALUMINA BASED CATALYST

(75) Inventors: Sylvie Lacombe, Saint Genis Laval (FR); Renaud Revel, Serpaize (FR); Patrick Briot, Pommier de Beaurepaire (FR); Eric Llido, Communay (FR); Patrick Euzen, Paris (FR); Carole Bobin, Marly le Roi (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 872 days.

(21) Appl. No.: 11/182,021

(22) Filed: Jul. 15, 2005

(65) Prior Publication Data
US 2006/0063955 A1 Mar. 23, 2006

(30) Foreign Application Priority Data
Jul. 15, 2004 (FR) .................................. 04 07899

(51) Int. Cl.
*C07C 2/08* (2006.01)
(52) U.S. Cl. .................. 585/532; 585/520; 585/533
(58) Field of Classification Search ................. 585/520, 585/532, 533
See application file for complete search history.

(56) References Cited

U.S. PATENT DOCUMENTS

| | | | |
|---|---|---|---|
| 5,051,386 A | 9/1991 | Ward et al. | |
| 5,342,814 A | 8/1994 | Peratello et al. | |
| 6,136,179 A * | 10/2000 | Sherwood et al. | ............ 208/109 |
| 6,733,657 B2 * | 5/2004 | Benazzi et al. | ............... 208/110 |
| 7,270,738 B2 * | 9/2007 | Euzen et al. | ............. 208/111.3 |

OTHER PUBLICATIONS

Sasol: "Pural, Catapal High Purity Aluminas" Jan. 2003, XP002326387.

* cited by examiner

*Primary Examiner*—In Suk Bullock
(74) *Attorney, Agent, or Firm*—Millen, White, Zelano & Branigan, P.C.

(57) ABSTRACT

An olefin oligomerization process employs a particular silica-alumina catalyst which comprises a non zeolitic support based on silica-alumina containing a quantity of more than 5% by weight and 95% by weight or less of silica ($SiO_2$) and has the following characteristics: a mean pore diameter, measured by mercury porosimetry, in the range 20 to 140 Å; a total pore volume, measured by mercury porosimetry, in the range 0.1 ml/g to 0.6 ml/g; a total pore volume, measured by nitrogen porosimetry, in the range 0.1 ml/g to 0.6 ml/g; a BET specific surface area in the range 100 to 550 $m^2/g$; a pore volume, measured by mercury porosimetry, included in pores with a diameter of more than 140 Å, of less than 0.1 ml/g; a pore volume, measured by mercury porosimetry, included in pores with a diameter of more than 160 Å, of less than 0.1 ml/g; a pore volume, measured by mercury porosimetry, included in pores with a diameter of more than 200 Å, of less than 0.1 ml/g; a pore volume, measured by mercury porosimetry, included in pores with a diameter of more than 500 Å, of less than 0.1 ml/g; and an X ray diffraction diagram containing at least the principal characteristic peaks of at least one of the transition aluminas included in the group composed of alpha, rho, khi, eta, gamma, kappa, theta and delta aluminas.

34 Claims, No Drawings

PROCESS FOR OLIGOMERIZING OLEFINS USING A SILICA-ALUMINA BASED CATALYST

BACKGROUND OF THE INVENTION

1. Field of the Invention

The invention relates to any process for oligomerizing olefins that can produce a fuel, for example the production of gasoline and/or kerosene from light olefinic feeds containing 2 to 8 carbon atoms, and in particular from light olefinic feeds containing a high proportion of propylene and/or butenes using an oligomerization catalyst based on silica-alumina with a reduced proportion of macropores. Compared with silica-alumina type catalysts already cited in the literature, the activity of the catalyst of the present invention is greater for the processes cited above.

2. Description of Related Art

Processes for oligomerizing light olefins for the production of olefins with a higher molecular weight are widely used in refining and in petrochemistry, with the aim of upgrading light olefins to bases for gasoline, kerosene or gas oil type fuels, or for solvents. Such oligomerization reactions are carried out in the presence of a catalyst, usually a solid catalyst. The olefins combine into dimers, trimers, tetramers, etc, the degree of oligomerization depending on the type of catalyst used and its temperature and pressure conditions of operation. The advantage of the oligomerization process over other processes which are well known in the field of refining and petrochemistry resulting in the same range of products resides in the fact that the compounds obtained contain no sulfur and contain very few aromatic compounds. The solid oligomerization catalysts often cited in the literature are catalysts of the solid phosphoric acid type (for example U.S. Pat. No. 2,913,506 and U.S. Pat. No. 3,661,801), silica-aluminas (for example U.S. Pat. No. 4,197,185, U.S. Pat. No. 4,544,791 and EP-A-0 463 673), zeolites (for example U.S. Pat. No. 4,642,404 and U.S. Pat. No. 5,284,989) and, to a lesser extent, heteropolyanions (for example Indian patent IN 170 903).

Solid phosphoric acid type catalysts have good activity as regards oligomerization, but they are difficult to manipulate, in particular when discharging, as they tend to increase in mass in the presence of olefins. Further, they cannot be regenerated. Heteropolyanion type catalysts produce a limited degree of polymerization as they do not tolerate high temperatures well. Zeolites produce oligomers with a more limited degree of branching than the preceding catalysts because of high form selectivity in the micropores. This is favorable to gas oil production, which has to have the right cetane index, but is not favorable to the production of gasoline which has to have a high octane number. Finally, silica-alumina type catalysts cited in the literature have fairly variable porosities which produce different characteristics. As an example, EP-A-0 463 673 claims, for the oligomerizing propylene, the use of an amorphous silica-alumina with a silica/alumina molar ratio between 30/1 and 500/1, a specific surface area between 500 and 1000 m²/g, a total pore volume between 0.3 and 0.6 ml/g, a mean pore diameter of at most about 1 nm, and with no pores with a diameter of more than 3 nm. U.S. Pat. No. 4,544,791 claims, for the oligomerizing $C_4$ olefins, the use of an amorphous silica-alumina with a silica content in the range 60% to 95% by weight, a specific surface area between 50 and 500 m²/g, and a total pore volume between 0.4 and 0.9 ml/g, but said silica-alumina does not exhibit an alumina phase in X ray diffraction.

DETAILED DESCRIPTION OF THE INVENTION

Through the remainder of the text, the term "oligomerization" means any addition reaction of one olefin with a further olefin.

The present invention concerns an olefin oligomerization process employing a particular silica-alumina catalyst, said catalyst comprising a non zeolitic support based on silica-alumina containing a quantity of more than 5% by weight up to not more than 95% by weight of silica ($SiO_2$) and having the following characteristics:

- a mean pore diameter, measured by mercury porosimetry, in the range 20 to 140 Å;
- a total pore volume, measured by mercury porosimetry, in the range 0.1 ml/g to 0.6 ml/g;
- a total pore volume, measured by nitrogen porosimetry, in the range 0.1 ml/g to 0.6 ml/g;
- a BET specific surface area in the range 100 to 550 m²/g;
- a pore volume, measured by mercury porosimetry, included in pores with a diameter of more than 140 Å, of less than 0.1 ml/g;
- a pore volume, measured by mercury porosimetry, included in pores with a diameter of more than 160 Å, of less than 0.1 ml/g;
- a pore volume, measured by mercury porosimetry, included in pores with a diameter of more than 200 Å, of less than 0.1 ml/g;
- a pore volume, measured by mercury porosimetry, included in pores with a diameter of more than 500 Å, of less than 0.1 ml/g, preferably less than 0.05 ml/g, more preferably less than 0.02 ml/g and still more preferably less than 0.01 ml/g; and
- an X ray diffraction diagram containing at least the principal characteristic peaks of at least one of the transition aluminas included in the group composed of alpha, rho, khi, eta, gamma, kappa, theta and delta aluminas.

Description of Oligomerization Catalyst

Characterization Techniques

In the following description, the term "specific surface area" means the BET specific surface area determined by nitrogen adsorption in accordance with ASTM D 3663-78 established using the BRUNAUER-EMMETT-TELLER method described in "The Journal of the American Society", 60, 309 (1938).

In the following description, the term "mercury volume of catalysts" means the volume measured by mercury porosimetric intrusion in accordance with ASTM D4284-83 at a maximum pressure of 4000 bars, using a surface tension of 484 dynes/cm and a contact angle for amorphous silica-alumina catalysts of 140°. The mean mercury diameter is defined as a diameter whereby all pores with a diameter less than that diameter constitute 50% of the pore volume ($V_{Hg}$) in a range 36 Å to 1000 Å. The wetting angle is taken to be 140°, following the recommendations in the work "Techniques de l'ingénieur, traité analyse et caractérisation", pages 1050-5, by Jean Charpin and Bernard Rasneur.

For greater accuracy, the value of the mercury volume in ml/g given in the text below corresponds to the total mercury volume in ml/g measured for the sample minus the value of the mercury volume in ml/g measured for the same sample for a pressure corresponding to 30 psi (about 2 bars). The mean mercury diameter is also defined, as the diameter for which all pores with a size less than this diameter constitute 50% of the total mercury pore volume.

To better characterize the pore distribution, we finally define the following criteria for the mercury pore distribution characteristics: volume V1 corresponds to the volume contained in pores for which the diameter is less than the mean diameter minus 30 Å. Volume V2 corresponds to the volume contained in pores with a diameter greater than or equal to the mean diameter minus 30 Å and less than the mean diameter plus 30 Å. Volume V3 corresponds to the volume contained in pores with a diameter greater than or equal to the mean diameter plus 30 Å. Volume V4 corresponds to the volume contained in pores with a diameter of less than the mean diameter minus 15 Å. Volume V5 corresponds to the volume contained in pores with a diameter greater than or equal to the mean diameter minus 15 Å and less than the mean diameter plus 15 Å. Volume V6 corresponds to the volume contained in pores with a diameter greater than or equal to the mean diameter plus 15 Å.

The pore distribution measured by nitrogen adsorption is determined by the Barrett-Joyner-Halenda model (BJH). The nitrogen adsorption-desorption isotherm using the BJH model is described in the periodical "The Journal of the American Society", 73, 373 (1951) by E P Barrett, L G Joyner and P P Halenda. In the description below, the term "nitrogen adsorption volume" means the volume measured for P/P0=0.99, the pressure at which it is assumed that the nitrogen has filled all of the pores. The mean nitrogen desorption diameter is defined as a diameter such that all of the pores below this diameter constitute 50% of the pore volume ($V_p$) measured on the nitrogen isotherm desorption branch.

The term "surface adsorption" means the surface measured on the adsorption isotherm branch. Reference should be made to the article by A Lecloux in "Mémoires de la Société Royale des Sciences de Liège", $6^{th}$ series, volume 1, section 4, pp 169-209 (1971).

The sodium content is measured by atomic absorption spectrometry.

X ray diffraction is a technique which can be used to characterize the catalysts of the invention. In the description below, the X ray analysis was carried out on powder with a Philips PW 1830 diffractometer operating in reflection mode and provided with a back monochromator using the CoKalpha radiation ($\lambda K_{\alpha 1}$=1.7890 Å, $\lambda I K_{\alpha 2}$=1.793 Å, $K_{\alpha 1}/K_{\alpha 2}$ intensity ratio=0.5). Reference should be made to the ICDD database, number 10-0425, for the X ray diffraction diagram of gamma alumina. In particular, the 2 most intense peaks are located at a position corresponding to a d in the range 1.39 to 1.40 Å and to a d in the range 1.97 Å to 2.00 Å. The term "d" is the interplanar spacing which is deduced from the angular position using the Bragg relationship ($2d_{(hkl)}*\sin(\theta)=n*\lambda$). The term "gamma alumina" as used in the remainder of the text means, inter alia, for example, an alumina included in the group composed of cubic gamma, pseudo-cubic gamma, tetragonal gamma, low crystallinity or poorly crystallized gamma, high surface area gamma, low surface area gamma, gamma from coarse boehmite, gamma from crystalline boehmite, gamma from low crystallinity or poorly crystallized boehmite, gamma from a mixture of crystalline boehmite and an amorphous gel, gamma from an amorphous gel, and gamma developing towards delta alumina. Reference should be made to the article by B C Lippens, J J Steggerda in "Physical and Chemical Aspects of Adsorbents and Catalysts" by E G Linsen (Ed), Academic Press, London, 1970, p 171-211 for the diffraction peaks for eta, delta and theta aluminas.

For the catalysts of the invention, the X ray diffraction diagram discloses a broad peak which is characteristic of the presence of amorphous silica.

Further, in the following text, the alumina compound may contain an amorphous fraction which is difficult to detect by XRD techniques. This therefore means that the alumina compounds used or described in the text may contain an amorphous or low crystallinity fraction.

The catalysts of the invention were analyzed by solid $^{27}$Al MAS NMR using a Brüker MSL 400 type spectrometer with a 4 mm probe. The sample rotation rate was of the order of 11 kHz. Aluminum NMR can potentially distinguish between three types of aluminum which have the following chemical displacements:

between 100 and 40 ppm, tetra-coordinated type aluminum, $Al_{IV}$;
between 40 and 20 ppm, penta-coordinated type aluminum, $Al_V$;
between 20 and −100 ppm, hexa-coordinated type aluminum, $Al_{VI}$;

The aluminum atom is a quadripolar nucleus. Under certain analytical conditions (weak radiofrequency field: 30 kHz, low pulse angle: $\pi/2$ and water-saturated sample), the magic angle spinning (MAS) NMR technique is a quantitative technique. The decomposition of MAS NMR spectra allows direct access to the quantity of the different species. The spectrum is calibrated as the chemical displacement with respect to a 1 M aluminum nitrate solution. The aluminum signal is at zero ppm. It was elected to integrate the signals between 100 and 20 ppm for $Al_{IV}$ and $Al_V$, which corresponds to area 1, and between 20 and −100 for $Al_{VI}$ which corresponds to area 2. In the following description, the term "proportion of octahedral $Al_{VI}$" means the following ratio: area 2/(area 1+area 2).

One method for characterizing the catalysts of the invention which may be used is transmission electron microscopy (TEM). For this, an electron microscope (of the Jeol 2010 or Philips Tecnai20F type, with optional scanning) is used, provided with an energy dispersion spectrometer (EDS) for X ray analysis (for example a Tracor or Edax). The EDS detector has to allow detection of light elements. The combination of the two tools, TEM and EDS, could combine imagery and local chemical analysis with good spatial resolution.

For this type of analysis, the samples are finely ground in a mortar; the powder is then included in resin to produce ultrafine sections with a thickness of about 70 nm. Such sections are collected on copper grids coated with a film of perforated amorphous carbon acting as a support. They are then introduced into the microscope for observation and analysis under high vacuum. With imagery, the sample zones are readily distinguished from the resin zones. A certain number of analyses are then carried out, a minimum of 10, preferably in the range 15 to 30, on different zones of the industrial sample. The size of the electron beam for zone analysis (approximately determining the size of the analyzed zones) is 50 nm in diameter as a maximum, preferably 20 nm, and more preferably 10, 5, 2 or 1 nm in diameter. In scanning mode, the analyzed zone will be a function of the size of the scanned zone and not the size of the beam, which is generally less.

The semi-quantitative processing of X ray spectra recorded using the EDS spectrometer can produce the relative concentration of Al and Si (as an atomic %) and the Si/Al ratio for each of the analyzed zones. The mean $Si/Al_m$ and the standard deviation $\sigma$ of this set of measurements can then be calculated. In the non limiting examples of the description which follows, the 50 nm probe was used to characterize the catalysts of the invention unless otherwise indicated.

The settled packing density (SPD) is measured as described in "Applied Heterogeneous Catalysis" by J F Le Page, J Cosyns, P Courty, E Freund, J-P Franck, Y Jacquin, B Juguin, C Marcilly, G Martino, J Miquel, R Montamal, A Sugier, H Van Landehchem, Technip, Paris, 1987. A suitably sized graduated cylinder is filled by successive additions and, between two successive additions, the catalyst is settled by shaking the cylinder to constant volume. This measurement is generally carried out on 1000 cm$^3$ of catalyst packed into a cylinder with a height to diameter ratio of close to 5:1. This measurement is preferably carried out using automated apparatus such as the Autotap® sold by Quantachrome®.

The acidity of the matrix is measured by IR. The IR spectra were recorded on a Nicolet Nexus-670 type interferometer at a resolution of 4 cm$^{-1}$ with Happ-Gensel type apodisation. The sample (20 mg) was pressed into a self-supporting pellet and placed in an in situ analytical cell (25° C. to 550° C., furnace offset from IR beam, high vacuum of 10$^{-6}$ mbars). The pellet diameter was 16 mm.

The sample was pre-treated as follows to eliminate physisorbed water and to partially dehydroxylate the catalyst surface to provide an image which was representative of the catalyst acidity when in operation:
  temperature rise from 25° C. to 300° C. over 3 hours;
  iso-temperature for 10 hours at 300° C.;
  temperature fall from 300° C. to 25° C. over 3 hours.

The basic probe (pyridine) was then adsorbed at saturated pressure at 25° C. then thermo-desorbed in the following stages:
  25° C. for 2 hours under high vacuum;
  100° C. for 1 hour under high vacuum;
  200° C. for 1 hour under high vacuum;
  300° C. for 1 hour under high vacuum.

A spectrum was recorded at 25° C. at the end of the pre-treatment and at each desorption stage in transmission mode with an accumulation time of 100 s. The spectra were recorded at iso-mass (and thus assumed to be iso-thickness) (exactly 20 mg). The number of Lewis sites is proportional to the surface area of the peak with a maximum near 1450 cm$^{-1}$, including shoulders. The number of Bronsted sites is proportional to the surface area of the peak with a maximum near 1545 cm$^{-1}$. The ratio of the number of Bronsted sites/number of Lewis sites is estimated to be equal to the ratio of the surface areas of the two peaks described above. In general, the surface areas of the peaks at 25° C. are used. This ratio B/L is generally calculated from the spectrum recorded at 25° C. at the end of pre-treatment.

Characteristics of Olefin Oligomerization Catalyst

The catalyst used in the process of the present invention is a non-zeolitic catalyst based on silica-alumina (i.e. comprising silica and alumina) with the following characteristics:
  the silica content (SiO$_2$, by weight) is more than 5% by weight up to not more than 95% by weight, preferably in the range of 10% to 80% by weight, preferably more than 20% by weight and less than 80% by weight and more preferably more than 25% by weight and less than 75% by weight. The silica content is advantageously in the range of 10% to 50% by weight;
  the cationic impurities content is generally less than 0.1% by weight, preferably less than 0.05% by weight and more preferably less than 0.025% by weight. The term "cationic impurities" means the total alkaline compound content;
  the anionic impurities content is generally less than 1% by weight, preferably less than 0.5% by weight and more preferably less than 0.1% by weight.

The silica-alumina used in the process of the invention is preferably a homogeneous silica-alumina on the micrometric scale and in which the cationic impurities content (for example Na$^+$) is less than 0.1% by weight, preferably less than 0.05% by weight and more preferably less than 0.025% by weight and the anionic impurities content (for example SO$_4^{2-}$ or Cl$^-$) is less than 1% by weight, preferably less than 0.5% by weight and more preferably less than 0.1% by weight.

Thus, any silica-alumina synthesis process known to the skilled person leading to a homogeneous silica-alumina on the micrometric scale and in which the cationic impurities content (for example Na$^+$) is collectively less than 0.1% by weight, preferably less than 0.05% by weight and more preferably less than 0.025% by weight and in which the anionic impurities content (for example SO$_4^{2-}$ or Cl$^-$) is collectively less than 1% by weight, preferably less than 0.05% by weight, is suitable for the preparation of the catalysts of the invention.

The catalysts used in the oligomerization process of the invention have the following characteristics:
  a mean catalyst pore diameter, measured by mercury porosimetry, in the range 20 to 140 Å, preferably in the range 40 to 120 Å and more preferably in the range 50 to 100 Å;
  preferably, the ratio between the volume V2, measured by mercury porosimetry, in the range between D$_{mean}$−30 Å and D$_{mean}$+30 Å, to the total pore volume, also measured by mercury porosimetry, is more than 0.6, preferably more than 0.7 and more preferably more than 0.8;
  preferably, the volume V3 in pores with diameters of more than D$_{mean}$+30 Å, measured by mercury porosimetry, is less than 0.1 ml/g, preferably less than 0.06 ml/g and more preferably less than 0.04 ml/g;
  preferably, the ratio between the volume V5 included between D$_{mean}$−15 Å and D$_{mean}$+15 Å, measured by mercury porosimetry, and the volume V2 included between D$_{mean}$−30 Å and D$_{mean}$+30 Å, measured by mercury porosimetry, is more than 0.6, preferably more than 0.7 and more preferably more than 0.8;
  preferably, the volume V6 in pores with diameters of more than D$_{mean}$+15 Å, measured by mercury porosimetry, is less than 0.2 ml/g, preferably less than 0.1 ml/g and more preferably less than 0.05 ml/g;
  the total pore volume, measured by mercury porosimetry, is in the range 0.1 ml/g to 0.6 ml/g, preferably in the range 0.20 to 0.50 ml/g;
  the total pore volume, measured by nitrogen porosimetry, is in the range 0.1 ml/g to 0.6 ml/g, preferably in the range 0.20 to 0.50 ml/g;
  the BET specific surface area is in the range 100 to 550 m$^2$/g, preferably in the range 150 to 500 m$^2$/g;
  the pore volume, measured by mercury porosimetry, included in pores with a diameter of more than 140 Å, is less than 0.1 ml/g, preferably less than 0.05 ml/g and more preferably less than 0.03 ml/g;
  the pore volume, measured by mercury porosimetry, included in pores with a diameter of more than 160 Å, is less than 0.1 ml/g, preferably less than 0.05 ml/g and more preferably less than 0.025 ml/g;
  the pore volume, measured by mercury porosimetry, included in pores with a diameter of more than 200 Å, is less than 0.1 ml/g, preferably less than 0.05 ml/g and more preferably less than 0.025 ml/g;
  the pore volume, measured by mercury porosimetry, included in pores with a diameter of more than 500 Å, is less than 0.01 ml/g, preferably less than 0.05 ml/g, more preferably less than 0.02 ml/g, and still more preferably less than 0.01 ml/g;

the X ray diffraction diagram contains at least the principal characteristic peaks of at least one of the transition aluminas included in the group composed of rho, khi, kappa, eta, gamma, theta and delta aluminas, and preferably at least the principal characteristic peaks of at least one of the transition aluminas included in the group composed of gamma, eta, theta and delta alumina, and more preferably at least the principal characteristic peaks of gamma and eta alumina, and still more preferably the diagram contains the peaks at a d in the range 1.39 to 1.40 Å and at a d in the range 1.97 Å to 2.00 Å.

Solid $^{27}$Al MAS NMR spectra of the catalysts exhibit two distinct peak masses. A first type of aluminum with a maximum resonating at about 10 ppm extends between −100 and 20 ppm. The position of the maximum suggests that these species are essentially of the $Al_{VI}$ type (octahedral). A second minor type of aluminum with a maximum resonating at about 60 ppm extends between 20 and 110 ppm. This can be decomposed into at least two species. The predominant species here corresponds to $Al_{IV}$ atoms (tetrahedral). For the catalysts used in the process of the present invention, advantageously, the proportion of octahedral $Al_{VI}$ is more than 50%, preferably more than 60%, and more preferably more than 70%.

In one implementation of the invention, the catalyst contains at least two silico-alumina zones, said zones having Si/Al ratios which are higher or lower than the overall Si/Al ratio determined by X ray fluorescence. Thus, a catalyst having a Si/Al ratio of 0.5 comprises two silico-alumina zones, one zone with a Si/Al ratio determined by TEM of less than 0.5 and the other zone with a Si/Al ratio determined by TEM in the range 0.5 to 2.5.

In a further implementation of the invention, the catalyst contains a single silico-alumina zone, said zone having a Si/Al ratio equal to the overall Si/Al ratio determined by X ray fluorescence and less than 6.

The acidity of the catalyst used in the process of the invention may advantageously, and without limiting the scope of the invention, be measured by IR monitoring of the thermodesorption of pyridine. In general, the ratio B/L, as described above, of the catalyst used in the process of the invention is in the range 0.05 to 6, preferably in the range 0.5 to 2.

The catalyst may optionally contain at least one metallic element selected from group IVB (for example titanium, zirconium, hafnium), group VB (for example vanadium, niobium, tantalum), group VIB (for example chromium, molybdenum, tungsten) and the first series of group VIII (Fe, Co, Ni) of the periodic table.

The amount of said metals may be up to 10% of the final catalyst weight.

The catalyst may optionally also contain silicon as the doping element deposited on the support.

Processes for Preparing the Silica-Alumina Catalyst Used in the Process of the Invention The Applicant has discovered that silica-alumina catalysts obtained by mixing, at any stage, an alumina compound which is partially soluble in an acidic medium with a silica compound which is completely soluble or with a completely soluble combination of alumina and hydrated silica, then shaping, followed by hydrothermal or thermal treatment to homogenize it on a micrometric scale or even on a nanometric scale, can produce a catalyst which is particularly active in the oligomerization processes of the invention. The term "partially soluble in an acidic medium" as used by the Applicant means that contact of the alumina compound prior to adding the completely soluble silica compound or the combination with an acidic solution, for example nitric acid or sulfuric acid, causes partial dissolution.

Silica Sources

The silica compounds used in accordance with the invention may be selected from the group formed by silicic acid, silicic acid sols, hydrosoluble alkaline silicates, cationic silicon salts, for example hydrated sodium metasilicate, Ludox® in its ammoniacal or alkaline form, or quaternary ammonium silicates. The silica sol may be prepared using any method known to the skilled person. Preferably, a solution of decationized orthosilicic acid is prepared from a hydrosoluble alkaline silicate by ion exchange over a resin.

Sources of Completely Soluble Silica-Aluminas

The completely soluble hydrated silica-aluminas used in the invention may be prepared by true co-precipitation under controlled stationary operating conditions (pH, concentration, temperature, mean residence time) by reaction of a basic solution containing silicon, for example in the form of sodium silicate, optionally with aluminum, for example in the form of sodium aluminate, with an acidic solution containing at least one aluminum salt, for example aluminum sulfate. At least one carbonate or $CO_2$ may optionally be added to the reaction medium.

The term "true co-precipitation" as used by the Applicant means a process in which at least one aluminum compound which is completely soluble in a basic medium or in an acidic medium as described above, and at least one silicon compound as described above, are brought into contact, simultaneously or sequentially, in the presence of at least one pre-cipitating and/or co-precipitating compound to obtain a mixed phase which is essentially constituted by hydrated silica-alumina which is optionally homogenized by intense agitation, shear, colloidal milling or by a combination of these individual operations. As an example, these hydrated silica-aluminas may have been prepared as described in the following American patents: U.S. Pat. No. 2,908,635; U.S. Pat. No. 3,423,332; U.S. Pat. No. 3,433,747; U.S. Pat. No. 3,451,947; U.S. Pat. No. 3,629,152 and U.S. Pat. No. 3,650,988.

Complete dissolution of the silica compound or the combination is determined approximately using the following method. A fixed quantity (15 g) of the silica compound or the hydrated combination is introduced into a medium at a fixed pH. Preferably, the concentration of solid with respect to a litre of suspension is 0.2 moles per litre. The pH of the dispersion solution is at least 12 and may be obtained using an alkaline source. Preferably, NaOH is advantageously used. The mixture is then mechanically stirred using a deflocculating turbine agitator for 30 minutes at 800 rpm. Once agitation is complete, the mixture is centrifuged for 10 minutes at 3000 rpm. The cake is separated from the supernatant liquid. The solution is filtered through a filter with a pore size of 4 and a diameter of 19 cm. Drying is then carried out followed by calcining the 2 fractions at 1000° C. A ratio R is determined by dividing the decanted mass by the mass of solid in suspension. The term "completely soluble" is applied to a ratio R of at least 0.9.

Sources of Alumina

The alumina compounds used in the invention are partially soluble in an acidic medium. They are completely or partially selected from the group of alumina compounds with general formula $Al_2O_3.n\,H_2O$. In particular, hydrated alumina compounds may be used, such as: hydrargillite, gibbsite, bayerite, boehmite, pseudo-boehmite and amorphous or essentially amorphous alumina gels. It is also possible to use dehydrated forms of said compounds which are constituted by transition aluminas and which comprise at least one of the phases in the following group: rho, khi, eta, gamma, kappa, theta, delta, which essentially differ from each other by the organization of their crystalline structure. Alpha alumina, commonly termed corundum, may be incorporated into the catalyst of the invention in small proportions.

This partial dissolution property is an important property of the invention, and is applicable to hydrated alumina powders, to spray dried hydrated alumina powders, to dispersions or suspensions of hydrated alumina or to any combination thereof, prior to any addition of a compound containing all or part of the silicon.

The partial dissolution of the alumina compound is evaluated as follows. A precise quantity of the powdered alumina compound or suspended alumina compound is introduced into a medium at a predetermined pH. The mixture is then mechanically stirred. Once agitation is complete, the mixture is left without agitation for 24 hours. Preferably, the concentration of solid $Al_2O_3$ with respect to one litre of suspension is 0.5 moles per litre. The pH of the dispersion solution is 2 and is obtained either by using $HNO_3$ or HCl or $HClO_4$. Preferably, $HNO_3$ is used. The distribution of sedimented and dissolved fractions is monitored by assaying the aluminum by UV absorption. The supernatants are ultrafiltered (polyethersulfone membrane, Millipore NMWL 30000) and digested in concentrated acid. The quantity of aluminum in the supernatant corresponds to the non-sedimented alumina compound and to the dissolved aluminum, and the ultrafiltered fraction corresponds to the dissolved aluminum alone. The quantity of sedimented particles is deduced from the theoretical concentration of aluminum in the dispersion (assuming that all of the solid which has been introduced is dispersed) and the quantities of boehmite actually dispersed and the aluminum in solution.

The alumina precursors used in the present invention are thus distinguished from those used in the case of true co-precipitation, which are entirely soluble in an acidic medium: cationic alumina salts, for example aluminum nitrate. The methods of the invention are distinguished from true co-precipitations since one of the elements, in this case the aluminum compound, is partially soluble.

To use the alumina, any compound of alumina with general formula $Al_2O_3$ n $H_2O$ may be used. Its specific surface area is in the range 150 to 600 $m^2/g$. In particular, it is possible to use hydrated alumina compounds such as: hydrargillite, gibbsite, bayerite, boehmite, pseudo-boehmite and amorphous or essentially amorphous alumina gels. It is also possible to use dehydrated forms of said compounds which are constituted by transition aluminas and which comprise at least one of the phases in the group: rho, khi, eta, gamma, kappa, theta, delta and alpha, which differ essentially in their crystalline structures. During heat treatments, these different forms may interchange in a complex sequence which depends on the operating conditions of the treatment. It is also possible to use small amounts of alpha alumina, commonly known as corundum.

More preferably, the aluminum hydrate $Al_2O_3$ n $H_2O$ used is boehmite, pseudo-boehmite and amorphous or essentially amorphous alumina gels. A mixture of said products in any combination may also be used.

Boehmite is generally described as an aluminum monohydrate with formula $Al_2O_3,nH_2O$ which encompasses a wide range of materials with varying degrees of hydration and organization the distinctions between which may be blurred: the most hydrated gelatinous boehmite, in which n may be greater than 2, pseudo-boehmite or micro-crystalline boehmite in which n is in the range 1 to 2, then crystalline boehmite and finally boehmite properly crystallized into large crystals with n close to 1. The morphology of aluminum monohydrate may vary widely between the two limiting forms, acicular and prismatic. A whole series of various forms may be used between these two forms: chains, boats, interlaced plates.

The preparation and/or shaping of aluminum hydrate may thus constitute the first step in preparing these catalysts. Many patents relate to the preparation and/or shaping of supports based on transition alumina from aluminum monohydrate: U.S. Pat. No. 3,520,654, U.S. Pat. No. 3,630,670, U.S. Pat. No. 3,864,461, U.S. Pat. No. 4,154,812, U.S. Pat. No. 4,313,923, DE 3 243 193 and U.S. Pat. No. 4,371,513.

Relatively pure aluminum hydrates may be used in the form of powders, which may be amorphous or crystalline, or crystalline containing an amorphous part. The aluminum hydrate may also be introduced in the form of aqueous suspensions or dispersions. The aqueous aluminum hydrate suspensions or dispersions employed in accordance with the invention may be capable of being gelled or coagulated. The aqueous dispersions or suspensions may also be obtained, as is well known to the skilled person, by peptization of aluminum hydrates in water or acidulated water.

The aluminum hydrate dispersion may be produced by any process which is known to the skilled person: in a "batch" reactor, a continuous mixer, a grinder, or a colloidal mill. Such a mixture may also be produced in a plug flow reactor and in particular in a static mixer. "Lightnin" reactors can be cited.

Further, the source of alumina may also be an alumina which has already undergone a treatment which can improve its degree of dispersion. As an example, it is possible to improve the dispersion of the alumina source by a preliminary homogenization treatment. The term "homogenization" means at least one of the homogenization treatments described in the text below.

The aqueous dispersions or suspensions of alumina which may be used are fine or ultrafine aqueous suspensions or dispersions of boehmites which are composed of particles with colloidal dimensions.

The fine or ultrafine boehmites used in accordance with the present invention may in particular have been obtained in accordance with patents FR-A-1 261 182 and FR-A-1 381 282 or European patent application EP-A-0 015 196.

It is also possible to use aqueous suspensions or dispersions obtained from pseudo boehmite, amorphous alumina gels, aluminum hydroxide gels or ultrafine hydrargillite gels.

Aluminum monohydrate may be purchased from a variety of commercial sources of alumina such as PURAL®, CATAPAL®, DISPERSAL®, DISPAL® sold by SASOL, or HIQ® sold by ALCOA, or using methods which are known to the skilled person: it may be prepared by partial dehydration of aluminum trihydrate using conventional methods, or it may be prepared by precipitation. When said aluminas are in the form of a gel, they are peptized by water or an acidulated solution. For precipitation, the source of the acid may, for example, be at least one of the following compounds: aluminum chloride, aluminum sulfate or aluminum nitrate. The source of basic aluminum may be selected from basic aluminum salts such as sodium aluminate or potassium aluminate.

Examples of precipitating agents which may be used are sodium hydroxide, sodium carbonate, potassium hydroxide and ammonia. The precipitating agents are selected so that the alumina source of the present invention and its agents are precipitated together.

Depending on the acidic or basic nature of the starting aluminum-based compound, the aluminum hydrate is precipitated using a base or an acid selected, for example, from hydrochloric acid, sulfuric acid, sodium hydroxide or a basic or acidic aluminum compound such as those cited above. The two reagents may be aluminum sulfate and sodium aluminate. As an example, the preparation of aluminum alpha-monohydrate using aluminum sulfate and sodium aluminate is described in U.S. Pat. No. 4,154,812.

Pseudo-boehmite may be prepared using the process described in U.S. Pat. No. 3,630,670 by reacting an alkaline aluminate solution with a mineral acid solution. Pseudo-boehmite may be prepared using the process described in U.S. Pat. No. 3,630,670 by reacting an alkaline aluminate solution with a mineral acid solution. It may also be prepared as described in FR-A-1 357 830.

Amorphous alumina gels may be prepared using the processes described in the article "Alcoa Paper No 19 (1972)", pages 9 to 12, and in particular by reacting an acid aluminate or an aluminum salt, by hydrolysis of aluminum alcoholates or by hydrolysis of basic aluminum salts.

The aluminum hydroxide gels may those prepared using the processes described in U.S. Pat. No. 3,268,295 and U.S. Pat. No. 3,245,919.

The aluminum hydroxide gels may also be those prepared using the processes described in WO-A-00/01617, by mixing a source of acidic aluminum and a base or a source of basic aluminum and an acid to precipitate an alumina monohydrate, the subsequent steps being:
  2—maturation;
  3—filtration;
  4—washing; and
  5—drying, these processes being characterized in that the mixing in step one is carried out without back-mixing.

Ultrafine hydrargillite may be prepared using the process described in U.S. Pat. No. 1,371,808, by heating, to a temperature in the range from ambient temperature to 60° C., alumina gels in the form of a cake and containing 0.1 monovalent acid ions with respect to the alumina, expressed as $Al_2O_3$ molecules.

It is also possible to use aqueous suspensions or dispersions of ultrapure boehmite or pseudo-boehmite prepared using a process in which an alkaline aluminate is reacted with a carbonic anhydride to form a precipitate of amorphous aluminum hydroxycarbonate, separating the precipitate obtained by filtering then washing it (the process has been described in U.S. Pat. No. 3,268,295).

Subsequently,
  a) in a first step, the washed amorphous aluminum hydroxycarbonate precipitate is mixed with a solution of an acid, a base or a salt or a mixture thereof; this mixture is made by pouring the solution onto the hydroxycarbonate, the pH of the medium so constituted being less than 11;
  b) in a second step, the reaction mixture is heated to a temperature of less than 90° C. for a time of at least 5 minutes; and
  c) in a third step, the medium resulting from the third step is heated to a temperature in the range 90° C. to 250° C.

The boehmite and pseudo-boehmite dispersions or suspensions obtained using this process have an alkali content of less than 0.005% expressed in the form of the ratio of the alkali metal oxide/$Al_2O_3$.

When very pure catalyst supports are to be made, ultrapure suspensions or dispersions of boehmites or pseudo-boehmites are preferably used, obtained using the process described above, or aluminum hydroxide gels which have been prepared by hydrolysis of aluminum alcoholates using a process of the type described in U.S. Pat. No. 2,892,858.

We shall now summarize the production process which produces such boehmite type aluminum hydroxide gels, obtained as a by-product in the production of alcohol by hydrolysis of an aluminum alcoholate or alkoxide (Ziegler synthesis). Ziegler alcohol synthesis reactions have been described in particular in U.S. Pat. No. 2,892,858. In that process, triethylaluminum is initially prepared from aluminum, hydrogen and ethylene, the reaction being carried out in two steps with a partial recycle of the triethylaluminum.

Ethylene is added in the polymerization step and the product obtained is then oxidized to aluminum alcoholate, the alcohols being obtained by hydrolysis.

The aluminum hydroxide gels may also be those which are prepared in accordance with the processes described in U.S. Pat. No. 4,676,928 and U.S. Pat. No. 6,030,599.

The hydrated alumina obtained as a by-product of the Ziegler reaction is that described in a bulletin from CONOCO dated 19 Jan. 1971.

The dimensions of the alumina particles constituting the source of alumina may vary widely. They are generally in the range 1 to 100 microns.

Catalyst Preparation Methods

The catalyst used in the process of the invention may advantageously be prepared using one of the methods described below.

As an example, one method for preparing a silica-alumina of the invention consists of preparing a solution of orthosilicic acid ($H_2SiO_4$, $H_2O$) decationized by ion exchange from a hydrosoluble alkaline silicate then simultaneously adding it to a cationic aluminum salt in solution, for example the nitrate, and to ammonia under controlled operating conditions; or adding the orthosilicic acid solution to the cationic aluminum salt in solution and co-precipitating the solution obtained with ammonia under controlled operating conditions, resulting in a homogeneous product. This silica-alumina hydrogel is mixed with an aluminum hydrate powder or suspension. After filtering and washing, drying with shaping and then calcining, preferably in air, in a rotary furnace, at high temperature and for a time sufficient to encourage interactions between alumina and silica, generally at least 2 hours, a catalyst with the characteristics of the invention is obtained.

Another method for preparing the silica-alumina of the invention consists of precipitating the alumina hydrate as above, filtering and washing it, then mixing it with aqueous orthosilicic acid to obtain a suspension, which is intimately homogenized by strong agitation and shearing. An Ultraturrax® turbine or a Staro® turbine may be used, or a colloidal mill, for example a Staro® colloidal mill. The homogeneous suspension is then dried by spraying as before, and calcined between 500° C. and 1200° C. for at least 3 hours: a silica-alumina catalyst which may be used in the process of the invention is obtained.

A further method of the invention consists of preparing a solution of decationized orthosilicic acid, as before, then simultaneously or consecutively adding it to an alumina compound, for example an aluminum hydrate in powdered form or in acidulated suspension. To increase the pore diameter of the final silica-alumina, at least one basic compound may optionally be added to the reaction medium. After deep homogenization of the suspension by agitation, optional adjustment of the dry matter content by filtering and optional re-homogenization, the product is dried with simultaneous or consecutive shaping, then calcined as above.

A further method which also forms part of the invention consists of preparing an aqueous suspension or dispersion of alumina, for example an aluminum monohydrate, then simultaneous or consecutively adding it to a silica compound, for example a sodium silicate. To increase the pore diameter of the final silica-alumina, at least one basic compound may optionally be added to the reaction medium. The catalyst is obtained by filtering and washing, optional washing with an ammoniacal solution to extract the residual sodium by ion exchange, and drying with simultaneous or consecutive shaping. After drying with shaping then calcining as before, a catalyst with the characteristics of the invention is obtained. The size of the alumina particles is preferably in the range 1 to 100 microns to obtain good homogenization of the silica-alumina catalyst of the invention.

To increase the diameter of the mesopores of the silica-alumina catalyst, it may be particularly advantageous, as disclosed in U.S. Pat. No. 4,066,574, to prepare an aqueous suspension or dispersion of alumina, for example an aluminum monohydrate, then to neutralize it with a basic solution, for example ammonia, then to simultaneously or consecutively add it to a silica compound, for example a decationized orthosilicic acid solution. After deep homogenization of the suspension by agitation, optional adjustment of the dry matter content by filtering and optional re-homogenization, the product is dried with simultaneous or consecutive shaping, then calcined as above. This method also constitutes a method of the invention.

In the description below of the methods above, the term "homogenization" is used to describe taking a product containing a solid fraction up into solution, for example a suspension, a powder, a filtered precipitate, then dispersing it with intense agitation. Homogenization of a dispersion is a process which is well known to the skilled person. Said homogenization may be carried out using any process which is known to the skilled person, for example in a batch reactor, a continuous mixer or a mill. Said mixing may be carried out in a plug reactor, in particular in a static reactor. "Lightnin" reactors may be cited. An Ultraturrax® turbine or a Staro® turbine may be used, or a colloidal mill, for example a Staro® colloidal mill. Commercially available IKA® colloidal mills may also be used.

In the methods cited above, it may optionally be desirable to add, during any step of the preparation, a small proportion of at least one stabilizing element selected from the group formed by zirconium and titanium. The stabilizing element is preferably added in the form of a soluble salt.

Catalyst Shaping

The catalyst may be obtained by shaping the silica-alumina using any technique which is known to the skilled person. Shaping may, for example, be carried out by extrusion, pelletization, by the oil drop coagulation method, by rotating plate granulation or by any other method which is known to the skilled person.

Shaping may also be carried out in the presence of various constituents of the catalyst and extrusion of the mineral paste obtained, by pelletization, by shaping into beads on a rotating bowl granulator or drum, by oil drop coagulation, oil-up coagulation or by any other known method for agglomeration of a powder containing alumina and optionally other ingredients selected from those mentioned above.

The catalysts used in the present invention have the shape of spheres or extrudates. However, it is advantageous that the catalyst be in the form of extrudates with a diameter in the range 0.5 to 5 mm, more particularly in the range 0.7 to 2.5 mm. The shapes are cylindrical (which may or may not be hollow), twisted cylinders, multilobes (2, 3, 4 or 5 lobes, for example), or rings. The cylindrical shape is preferably used, but any other form may be used.

Further, said catalysts used in the present invention may have been treated, as is well known to the skilled person, by additives to facilitate shaping and/or to improve the final mechanical properties of the silica-alumina catalysts. Examples of additives which may be cited are cellulose, carboxymethyl cellulose, carboxyethyl cellulose, tall oil, xanthan gums, surfactants, flocculating agents such as polyacrylamides, carbon black, starches, stearic acid, polyacrylic alcohol, polyvinyl alcohol, biopolymers, glucose, polyethylene glycols, etc.

Partial adjustment of the characteristic porosity of the catalysts of the invention is carried out during this step for shaping the catalyst particles.

Shaping may be carried out using catalyst shaping techniques which are known to the skilled person, such as extrusion, pelletization, spray drying or drageification.

Water may be added or removed to adjust the viscosity of the paste to be extruded. This step may be carried out at any stage of the mixing step.

To adjust the solid material content of the paste to be extruded to render it extrudable, it is also possible to add a mainly solid compound, preferably an oxide or hydrate. Preferably, a hydrate is used, more preferably an aluminum hydrate. The loss on ignition of the hydrate is more than 15%.

The amount of acid added on mixing before shaping is less than 30%, preferably in the range 0.5% to 20% by weight of the anhydrous mass of silica and alumina engaged in the synthesis.

Extrusion may be carried out using any conventional tool which is on the market. The paste issuing from the mixing step is extruded through a die, for example using a piston or a single or twin extrusion screw. This extrusion step may be carried out using any method which is known to the skilled person.

The catalyst extrudates of the invention generally have a crush strength of at least 70 N/cm, more preferably 100 N/cm or more.

Drying and Calcining the Catalyst

Drying is carried out using any technique which is known to the skilled person.

To obtain the catalyst used in the process of the present invention, it is preferable to calcine in the presence of molecular oxygen, for example by flushing with air, at a temperature of 1100° C. or less. At least one calcining step may be carried out after any one of the preparation steps. This treatment may, for example, be carried out in a traversed bed, swept bed or in a static atmosphere. As an example, the furnace used may be a rotary furnace or a vertical furnace with radial flow layers. The calcining conditions—temperature and duration—principally depend on the maximum catalyst service temperature; the preferred calcining conditions are more than one hour at 200° C. and less than one hour at 100° C. Calcining may be carried out in the presence of steam. Final calcining may optionally be carried out in the presence of an acidic or basic vapor. As an example, calcining may be carried out in a partial pressure of ammonia.

Post-Synthesis Treatments

Post-synthesis treatments may be carried out to improve the properties of the support, in particular its homogeneity as defined above.

In one preferred implementation, the post-synthesis treatment is a hydrothermal treatment. The hydrothermal treatment is carried out using any technique which is known to the skilled person. The term "hydrothermal treatment" means contact at any stage of the manufacture of the mixed support with water in the vapor phase or in the liquid phase. The term "hydrothermal treatment" encompasses maturation, steam treatment, autoclaving, calcining in moist air, and rehydration. Without restricting the scope of the invention, such a treatment may have the effect of rendering the silica component mobile.

According to the invention, maturation may take place before or after shaping. In accordance with the invention, steam treatment is carried out in a furnace in the presence of water vapor. The temperature during steam treatment may be in the range 600° C. to 1100° C., preferably over 700° C. for a period in the range 30 minutes to 3 hours. The steam content is more than 20 g of water per kg of dry air and preferably more than 40 g of water per kg of dry air, more preferably more than 100 g of water per kg of dry air. Such a treatment may if required completely or partially replace the calcining treatment.

According to the invention, the support may then optionally undergo hydrothermal treatment in a confined atmosphere. The term "hydrothermal treatment in a confined atmosphere" means treatment by using an autoclave in the presence of water at a temperature which is above ambient temperature.

During said hydrothermal treatment, the shaped silica-alumina may be treated in different manners. Thus, the silica-alumina may be impregnated with acid prior to its entry into the autoclave, silica-alumina autoclaving being carried out either in the vapor phase or in the liquid phase; said vapor or liquid phase in the autoclave may or may not be acidic. Impregnation prior to autoclaving may or may not be acidic. Said impregnation prior to autoclaving may be carried out dry or by immersing the silica-alumina in an aqueous acidic solution. The term "dry impregnation" means bringing the alumina into contact with a volume of solution which is less than or equal to the total pore volume of the treated alumina. Preferably, dry impregnation is carried out.

The autoclave is preferably a rotating basket autoclave such as that defined in EP-A-0 387 109.

The temperature during autoclaving may be in the range 100° C. to 250° C. for a period in the range 30 minutes to 3 hours.

One preferred method of the invention consists of depositing silica onto the shaped catalyst on the calcined or non calcined precursor, preferably calcined. To this end, for example, a solution of a silicone or silicone oil emulsion type silicon compound may be used which will be impregnated onto the preformed precursor. Subsequently, drying may be carried out at 120° C., for example, and calcining may then be carried out, as is preferable, in air in a traversed bed, for example at 500° C. for 4 hours.

Many sources of silicon may be used. It is possible to use ethyl orthosilicate $Si(OEt)_4$, siloxanes, polysiloxanes, silicones, silicone emulsions, halogenated silicates such as ammonium fluorosilicate $(NH_4)_2SiF_6$ or sodium fluorosilicate $Na_2SiF_6$. The silica may, for example, be added by impregnating ethyl silicate in solution in a water/alcohol mixture. The silica may, for example, be added by impregnating a silicone type silicon compound or silicic acid suspended in water.

It is also optionally possible to add to the silica-alumina, at any step in the preparation, precursors of transition metals selected from group IVB (titanium, zirconium, hafnium), group VI (vanadium, niobium, tantalum), group VIB (chromium, molybdenum, tungsten) and the first series of group VIII (Fe, Co, Ni). The amount of said metals may be up to 10% by weight of the final catalyst.

Description of the Oligomerization Process

The process of the invention is a process for oligomerizing olefins to produce a fuel, for example the production of gasoline and/or kerosene from light olefinic feeds containing between 2 and 8 carbon atoms, in particular from light olefinic feeds containing a high proportion of propylene and/or butenes using an oligomerization catalyst based on silica-alumina with a reduced number of macropores.

Thus, the invention concerns a process for oligomerizing olefins in which the oligomerization catalyst comprises a non zeolitic support based on silica-alumina containing a quantity of more than 5% by weight and 95% by weight or less of silica ($SiO_2$) and has the following characteristics:

a mean pore diameter, measured by mercury porosimetry, in the range 20 to 140 Å;

a total pore volume, measured by mercury porosimetry, in the range 0.1 ml/g to 0.6 ml/g;

a total pore volume, measured by nitrogen porosimetry, in the range 0.1 ml/g to 0.6 ml/g;

a BET specific surface area in the range 100 to 550 $m^2/g$;

a pore volume, measured by mercury porosimetry, included in pores with a diameter of more than 140 Å, of less than 0.1 ml/g;

a pore volume, measured by mercury porosimetry, included in pores with a diameter of more than 160 Å, of less than 0.1 ml/g;

a pore volume, measured by mercury porosimetry, included in pores with a diameter of more than 200 Å, of less than 0.1 ml/g;

a pore volume, measured by mercury porosimetry, included in pores with a diameter of more than 500 Å, of less than 0.1 ml/g, preferably less than 0.05 ml/g, more preferably less than 0.02 ml/g and still more preferably less than 0.01 ml/g; and an X ray diffraction diagram containing at least the principal characteristic peaks of at least one of the transition aluminas included in the group composed of alpha, rho, khi, eta, gamma, kappa, theta and delta aluminas.

Compared with prior art catalysts, the catalyst of the present invention has improved activity in the olefin oligomerization processes cited above, and is easy to use.

Feeds

The olefins may, for example, derive from a catalytic cracking unit and/or from a steam cracking unit and/or from a paraffin dehydrogenation unit and/or from a unit for the polymerizing dehydration of methanol to water and light olefins and/or from any other source of light olefins.

The olefinic cut sent to the oligomerization reactor containing the catalyst of the invention is preferably free of impurities such as water, sulfur-containing derivatives, basic nitrogen-containing derivatives, before being introduced into the oligomerization reactor.

The olefinic cut may be an olefinic C4 cut, which normally comprises more than 90% by weight of isobutane, n-butane, 1-butene, 2-butenes, isobutene and possibly a small quantity of butadiene. The butadiene is generally eliminated upstream of the oligomerization step by a selective hydrogenation process.

The olefinic cut may be an olefinic C3-C4 cut. The composition of the C3-C4 olefinic cut is highly variable, depending on its provenance. It may comprise between about 20% and 50% by weight of propylene and propane, between about 50% and 80% by weight of isobutane, n-butane, 1-butene, 2-butenes, isobutene, and possibly a small quantity of butadiene. The butadiene is generally eliminated upstream of the oligomerization step by a selective hydrogenation process.

The olefinic cut may be an olefinic C3 cut. It normally comprises at least 90% by weight of propylene, propane.

In all of the oligomerization processes of the invention, the exothermicity of the reaction may be managed by recycling at least a portion of the unconverted effluent, which in particular contains paraffins which have not been transformed during the reaction, to the oligomerization reactor, and/or the feed may be diluted by adding paraffins from another source, said paraffins being of the same molecular weight and/or heavier than the olefinic feed, said paraffins being aliphatic or cyclic.

In all of the processes resulting in the formation of gasoline and/or kerosene, and/or more generally an olefinic cut with a boiling point commencing at a temperature of more than 150° C., said olefinic cuts obtained at the end of the process may also be partially or completely hydrogenated.

Implementations

First Implementation: Selective Oligomerization

The catalyst of said invention is particularly impressive in the process in which an olefinic C4 cut undergoes oligomerization, limiting the overall conversion of n-butenes to less than 10%, preferably to less than 5%, while more than 90% of the quantity of isobutene is converted, preferably more than 95%. The isobutene is more than 90% converted into dimers and trimers. Subsequently, the oligomerization effluent undergoes distillation so that the recovered fractions (light effluent) contain more than 90% by weight of butane, isobutane and butenes which have not reacted during the oligomerization, at least a portion of said fraction then supplying an alkylation unit or a hydration unit, for example, while the other fraction constituted by the oligomers obtained is used as a gasoline base, optionally after partial or complete hydrogenation.

The process cited above will henceforth herein be termed "selective oligomerization".

The oligomerization reaction is carried out at a temperature between 30° C. and 300° C., at a pressure between about 0.1 and 20 MPa and with a volume of hydrocarbon feed per volume of catalyst per hour in the range 0.05 to 5 $h^{-1}$. Preferably, the temperature is between 40° C. and 160° C., and the pressure is between 2 and 7 MPa, to ensure that the reaction is carried out in the liquid phase or at least in a homogeneous phase, and the volume of hydrocarbon feed per volume of catalyst per hour is preferably in the range 0.8 to 2.5 $h^{-1}$.

The reactor may be a fixed bed, fluidized bed or moving bed reactor. Preferably, it is a fixed bed reactor.

Optionally, the oligomers obtained may be re-injected into a supplemental oligomerization reactor containing, for example, the oligomerization catalyst which is described above, to increase the chain length of the oligomers and thus attain the kerosene cut, or more generally an olefinic cut with an initial boiling point at a temperature of more than 150° C.

Optionally, the light oligomerization effluent, i.e. the C4 cut, may be introduced into a hydroisomerization reactor to hydroisomerize a portion of the 1-butene which is not converted into 2-butene, to approach thermodynamic equilibrium. The other constituents of the effluent are thus not significantly converted during the hydroisomerization step. The conversion of 1-butene to 2-butene is very useful if the C4 fraction obtained may then be introduced into a reactor for aliphatic alkylation over hydrofluoric acid, the products obtained by alkylation of 2-butene with isobutane having a better octane number than the alkylate obtained from 1-butene.

Given the exothermic nature of the oligomerization reaction, the quantity of isobutene in the hydrocarbon feed supplying the oligomerization reactor is preferably less than 35% by weight, more preferably less than 15% by weight, this optionally having been obtained by diluting the feed, for example with butane or isobutene or raffinate from the oligomerization unit.

Second Oligomerization Mode

The catalyst described in said invention is also particularly impressive in the process consisting of subjecting a C4 olefinic cut or C3-C4 olefinic cut to oligomerization so that a portion of the butenes contained in the feed are converted into dimers or trimers, used subsequently as a gasoline base. In the case of this process, less than 80% of the butenes are converted and at least 80%, preferably at least 90%, of the isobutene is converted. This process can maximize the quantity of gasoline while minimizing the quantity of kerosene formed.

In the oligomerization reactor, the temperature is between 40° C. and 250° C., preferably between 50° C. and 200° C., and the pressure is between 0.1 and 10 MPa, preferably between 0.1 and 5 MPa, and the quantity of hydrocarbon feed per volume of catalyst per hour is in the range 0.05 to 5 $h^{-1}$, preferably in the range 0.8 to 2.5 $h^{-1}$. The reactor may be a fixed bed, fluidized bed or moving bed reactor. Preferably, a fixed bed reactor is used.

In a variation of this implementation of the process, the feed is an olefinic feed from which the isobutene has been partially or completely eliminated, for example using an etherification unit upstream of the oligomerization unit by selectively reacting the isobutene with an alcohol, for example methanol or ethanol, without converting n-butene, or using a selective oligomerization unit such as that described above upstream of the oligomerization unit. The oligomers produced then have fewer branches than those obtained by treating the complete cut including isobutene.

Third Implementation

A third implementation of the process of the invention consists of subjecting an olefinic C4 cut optionally containing traces of propylene to oligomerization such that the major portion of the butenes contained in the feed is converted into dimers or trimers which are then used as a gasoline base. In this process, at least 90% of the 1-butene, at least 80% of the 2-butenes, at least 97% of the isobutene and at least 80% of the propylene are converted. This process can maximize the quantity of gasoline without producing kerosene.

The olefinic C4 cut usually comprises isobutane, n-butane, 1-butene, 2-butene, isobutene and possibly a small quantity of butadiene. The butadiene is generally eliminated upstream of the oligomerization step by a selective hydrogenation step to avoid polymerization reactions which would render the catalyst inactive.

Said process comprises the following steps:

first oligomerization step: an olefinic C4 or C3-C4 cut is treated in a first oligomerization reactor in which the overall conversion of n-butenes in the feed is less than 45% and the isobutene conversion is more than 80%, preferably more than 85%, the oligomers obtained being more than 80% dimers and trimers;

the effluent from the first oligomerization step is sent to a fractionation column to recover a first fraction containing isobutene and unconverted n-butenes and a second fraction consisting of 90% dimers and trimers from the oligomerization reaction;

second oligomerization step: the first recovered fraction is introduced into a second oligomerization reactor in which most of the olefins are converted into dimers and trimers, i.e. at least 50% of n-butenes are converted; preferably, at least 75% of the 1-butene and at least 55% of the 2-butenes are converted; and the effluent from the second oligomerization step is sent to the fractionation column associated with the first oligomerization reactor or to a second column to separate the gasoline or kerosene from unconverted C4 compounds.

In the oligomerization reactors, the temperature is between 40° C. and 250° C., preferably between 45° C. and 200° C., and the pressure is between 0.1 and 10 MPa, preferably between 0.1 and 5 MPa, and the quantity of hydrocarbon feed per volume of catalyst per hour is between 0.05 and 5 $h^{-1}$, preferably between 0.8 and 2.5 $h^{-1}$. The reactor may be a fixed bed, fluidized bed or moving bed reactor. Preferably, it is a fixed bed reactor.

Preferably, in the second oligomerization reactor, the operating conditions are more severe than in the first reactor.

The same process may be applied to a C3-C4 olefinic feed.

Fourth Implementation

The catalyst of said invention is also particularly impressive in the process consisting of subjecting an olefinic C4 cut or an olefinic C3-C4 cut to oligomerization such that the major portion of the butenes contained in the feed are converted, to form a gasoline base and a kerosene base. In this process, at least 90% of the 1-butene, at least 80% of the 2-butenes and at least 97% of the isobutene are converted. The olefinic C4 cut normally essentially comprises isobutane, n-butane, 1-butene, 2-butene, isobutene and possibly a small quantity of butadiene. The olefinic C3C4 cut also contains propane and propylene.

In the oligomerization reactor, the temperature is between 60° C. and 250° C., preferably between 100° C. and 200° C., and the pressure is between 0.1 and 10 MPa, preferably between 0.1 and 5 MPa, and the quantity of hydrocarbon feed per volume of catalyst per hour is between 0.05 and 5 $h^{-1}$, preferably between 0.8 and 2.5 $h^{-1}$.

The reactor may be a fixed bed, fluidized bed or moving bed reactor. Preferably, it is a fixed bed reactor.

Fifth Implementation

The catalyst of said invention is also particularly impressive in the process in which an olefinic C3 cut undergoes oligomerization such that the major portion of the propylene contained in the feed is converted, i.e. at least 80% of the propylene contained in the feed is converted, to form a gasoline base and a kerosene base.

The olefinic C3 cut normally comprises at least 90% propylene and propane.

In the oligomerization reactor, the temperature is between 30° C. and 300° C., the pressure is between about 0.1 and 20 MPa, and the quantity of hydrocarbon feed per volume of catalyst per hour is between 0.05 and 5 $h^{-1}$. Preferably, the temperature is between 40° C. and 160° C., the pressure is between 2 and 7 MPa and the volume of hydrocarbon feed per volume of catalyst per hour is preferably between 0.8 and 2.5 $h^{-1}$.

The reactor may be a fixed bed, fluidized bed or moving bed reactor. Preferably, it is a fixed bed reactor.

The following examples illustrate the present invention without limiting its scope.

Example 1

Silica-Alumina not in Accordance with the Invention (SA1)

The catalyst SA1 has the following characteristics:
the silica-alumina catalyst composition is 89.3% $Al_2O_3$ and 10.7% $SiO_2$;
the BET surface area is 370 $m^2/g$;
the total pore volume, measured by nitrogen adsorption, is 0.457 ml/g;
the mean pore diameter, measured by mercury porosimetry, is 48 Å;
the ratio between the volume V2 measured by mercury porosimetry between $D_{mean}$−30 Å and $D_{mean}$+30 Å to the total mercury volume is 0.92;
the volume V3, measured by mercury porosimetry, in pores with diameters of more than $D_{mean}$+30 Å is 0.042 ml/g;
the volume V6, measured by mercury porosimetry, in pores with diameters of more than $D_{mean}$+15 Å is 0.013 ml/g;
the pore volume, measured by mercury porosimetry, in pores with diameters of more than 140 Å is 0.02 ml/g;
the pore volume, measured by mercury porosimetry, in pores with diameters of more than 160 Å is 0.02 ml/g;
the pore volume, measured by mercury porosimetry, in pores with diameters of more than 200 Å is 0.01 ml/g;
the pore volume, measured by mercury porosimetry, in pores with diameters of more than 500 Å is 0.004 ml/g;
the X ray diffraction diagram contains none of the principal characteristic peaks of gamma alumina;
the B/L ratio for the catalyst is 1;
the settled packing density of the catalyst is 0.72 $g/cm^3$;
the atomic sodium content is 300+/−20 ppm. The atomic sulfur content is 2500 ppm.

Solid $^{27}Al$ MAS NMR spectra of the catalysts showed two distinct peak complexes. A first type of aluminum for which the maximum resonates at about 10 ppm extends between −100 and 20 ppm. The position of the maximum suggests that these species are essentially of the $Al_{VI}$ type (octahedral). A second major type of aluminum with a maximum resonating at about 60 ppm extends between 20 and 100 ppm. The predominant species here corresponds to $Al_{IV}$ atoms (tetrahedral). The proportion of octahedral $Al_{VI}$ species is 35%.

The catalyst contains a single silica-alumina zone with a Si/Al ratio, determined by TEM microprobe, of 4.3.

Example 2

Preparation and Shaping of a Silica-Alumina in Accordance with the Invention (SA2)

The aluminum hydroxide powder was prepared using the process described in WO-A-00/01617. The mean particle size for the aluminum hydroxide particles, measured by laser granulometry, was 40 microns. This powder was mixed with a silica sol prepared by exchange on a decationizing resin, then filtered through a resin with a porosity of 2. The concentrations of silica sol and aluminum hydroxide powder were adjusted to obtain a final composition of 70% $Al_2O_3$ and 30% $SiO_2$. Shaping was carried out in the presence of 15% nitric acid with respect to the anhydrous product. Mixing was carried out using a Z arm mixer. Extrusion was carried out by passing the paste through a die provided with 1.4 mm diameter orifices. The extrudates obtained were dried at 150° C. then calcined at 550° C.

The catalyst had the following characteristics:
the silica-alumina catalyst composition is 85.3% $Al_2O_3$ and 14.7% $SiO_2$;
the BET surface area is 430 $m^2/g$;
the total pore volume, measured by nitrogen adsorption, is 0.24 ml/g;
the mean pore diameter, measured by mercury porosimetry, is 46 Å;
the ratio between the volume V2 measured by mercury porosimetry between $D_{mean}$−30 Å and $D_{mean}$+30 Å to the total mercury volume is 0.7;
the volume V3, measured by mercury porosimetry, in pores with diameters of more than $D_{mean}$+30 Å is 0.07 ml/g;

the volume V6, measured by mercury porosimetry, in pores with diameters of more than $D_{mean}+15$ Å is 0.08 ml/g;

the pore volume, measured by mercury porosimetry, in pores with diameters of more than 140 Å is 0.06 ml/g;

the pore volume, measured by mercury porosimetry, in pores with diameters of more than 160 Å is 0.051 ml/g;

the pore volume, measured by mercury porosimetry, in pores with diameters of more than 200 Å is 0.047 ml/g;

the pore volume, measured by mercury porosimetry, in pores with diameters of more than 500 Å is 0.03 ml/g;

the B/L ratio for the catalyst is 1.1;

the settled packing density of the catalyst is 0.80 g/cm$^3$;

the X ray diffraction diagram contains the principal characteristic peaks of gamma alumina; in particular, it contains peaks with a d in the range 1.39 Å to 1.40 Å and a d in the range 1.97 Å to 2.00 Å;

the atomic sodium content is 40+/−20 ppm. The atomic sulfur content is 200 ppm.

Solid $^{27}$Al MAS NMR spectra of the catalysts showed two distinct peak complexes. A first type of aluminum for which the maximum resonates at about 10 ppm extends between −100 and 20 ppm. The position of the maximum suggests that these species are essentially of the $Al_{VI}$ type (octahedral). A second major type of aluminum with a maximum resonating at about 60 ppm extends between 20 and 100 ppm. This complex could be resolved into at least two species. The predominant species here corresponds to $Al_{IV}$ atoms (tetrahedral). The proportion of octahedral $Al_{VI}$ species is 65%.

The catalyst contains two silica-alumina zones, said zones having Si/Al ratios which are higher or lower than the overall Si/Al ratio determined by X ray fluorescence. One of the zones has a Si/Al ratio, determined by TEM, of 4.35 and the other zone has a Si/Al ratio, determined by TEM, of 1.75.

Example 3

Catalytic Evaluation of Silica-Aluminas SA1 and SA2 in a High Conversion Oligomerization Process An olefinic C4 cut from a steam cracking unit underwent a selective hydrogenation treatment to eliminate butadiene, then was dried over a type 13x molecular sieve to eliminate traces of sulfur and water.

The composition of the feed after said treatments was as follows:

| Composition of feed (weight %) | |
|---|---|
| Isobutane | 1.54 |
| n-butane | 7.74 |
| Isobutene | 39.89 |
| 1-butene | 28.64 |
| Σ 2-butenes | 22.18 |

This feed was sent to an isothermal oligomerization reactor containing the silica-alumina based catalyst SA1 or SA2. The operating conditions were as follows:

| Catalyst | SA1 | SA2 |
|---|---|---|
| Pressure | 6.0 MPa | 6.0 MPa |
| Temperature | 130° C. | 130° C. |
| HSV | 2 h$^{-1}$ | 2 h$^{-1}$ |

At the outlet from the oligomerization reactor, the composition by weight of the effluent was as follows:

| Catalyst | SA1 | SA2 |
|---|---|---|
| Composition of effluent (weight %) | | |
| Isobutane | 2.56 | 3.64 |
| n-butane | 7.89 | 7.89 |
| Isobutene | — | — |
| 1-butene | 0.72 | 0.26 |
| Σ 2-butenes | 12.35 | 6.81 |
| C5+ polymer | 76.48 | 81.40 |

The use of catalyst SA2 resulted in a yield of C5+ polymer that was higher than with catalyst SA1.

Example 4

Catalytic Evaluation of Silica-Aluminas SA1 and SA2 in a Moderate Conversion Oligomerization Process An olefinic C4 cut from a steam cracking unit underwent a selective hydrogenation treatment to eliminate butadiene, then was dried over a type 13x molecular sieve to eliminate traces of sulfur and water. The composition of the feed after said treatments was as follows:

| Composition of feed (weight %) | |
|---|---|
| Isobutane | 1.50 |
| n-butane | 6.63 |
| Isobutene | 49.48 |
| 1-butene | 27.86 |
| Σ 2-butenes | 14.53 |

This feed was sent to an isothermal oligomerization reactor containing the silica-alumina based catalyst SA1 or SA2. The operating conditions were as follows:

| Catalyst | SA1 | SA2 |
|---|---|---|
| Pressure | 2.5 MPa | 2.0 MPa |
| Temperature | 85° C. | 80° C. |
| HSV | 0.5 h$^{-1}$ | 0.5 h$^{-1}$ |

At the outlet from the oligomerization reactor, the composition by weight of the effluent was as follows:

| Catalyst | SA1 | SA2 |
|---|---|---|
| Composition of effluent (weight %) | | |
| Isobutane | 1.61 | 1.57 |
| n-butane | 6.60 | 6.64 |
| Isobutene | 0.48 | 0.41 |
| 1-butene | 23.41 | 22.90 |
| Σ 2-butenes | 18.92 | 19.01 |
| C5+ polymer | 48.97 | 49.47 |

The use of catalyst SA2 resulted in a yield of C5+ polymer that was higher than with catalyst SA1.

Example 5

Catalytic Evaluation of Silica-Aluminas SA1 and SA2 in a High Conversion Oligomerization Process An olefinic C4 cut from a catalytic cracking unit underwent a selective hydrogenation treatment to eliminate butadiene, then was dried over a type 13x molecular sieve to eliminate traces of sulfur and water.

The composition of the feed after said treatments was as follows:

| Composition of feed (weight %) | |
|---|---|
| Isobutane | 29.10 |
| n-butane | 11.45 |
| Isobutene | 14.22 |
| 1-butene | 14.20 |
| Σ 2-butenes | 31.03 |

This feed was sent to an isothermal oligomerization reactor containing the silica-alumina based catalyst SA1 or SA2. The operating conditions were as follows:

| Catalyst | SA1 | SA2 |
|---|---|---|
| Pressure | 6.0 MPa | 6.0 MPa |
| Temperature | 125° C. | 125° C. |
| HSV | 2 h$^{-1}$ | 2 h$^{-1}$ |

At the outlet from the oligomerization reactor, the composition by weight of the effluent was as follows:

| Catalyst | SA1 | SA2 |
|---|---|---|
| Composition of effluent (weight %) | | |
| Isobutane | 29.30 | 29.42 |
| n-butane | 11.45 | 11.45 |
| Isobutene | 0.31 | 0.08 |
| 1-butene | 4.03 | 2.41 |
| Σ 2-butenes | 36.25 | 23.15 |
| C5+ polymer | 18.66 | 33.49 |

The use of catalyst SA2 resulted in a yield of C5+ polymer that was higher than with catalyst SA1.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosure of all applications, patents and publications, cited herein and of corresponding French application No. 04/07.899, filed Jul. 15, 2004 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. In a process comprising catalytically oligomerizing a feed comprising at least one olefin the improvement wherein the oligomerization catalyst comprises a non zeolitic support based on silica-alumina containing a quantity of more than 5% by weight up to not more than 95% by weight of silica, ($SiO_2$) and said catalyst has the following characteristics:
    a mean pore diameter, measured by mercury porosimetry, in the range of 20 to 140 Å;
    a total pore volume, measured by mercury porosimetry, in the range of 0.1 ml/g to 0.6 ml/g;
    a total pore volume, measured by nitrogen porosimetry, in the range gf 0.1 ml/g to 0.6 ml/g;
    a BET specific surface area in the range of 100 to 550 m$^2$/g;
    a pore volume, measured by mercury porosimetry, included in pores with a diameter of more than 140 Å, of less than 0.1 ml/g;
    a pore volume, measured by mercury porosimetry, included in pores with a diameter of more than 160 Å, of less than 0.1 ml/g;
    a pore volume, measured by mercury porosimetry, included in pores with a diameter of more than 200 Å, of less than 0.1 ml/g;
    a pore volume, measured by mercury porosimetry, included in pores with a diameter of more than 500 Å, of less than 0.1 ml/g,
    an X ray diffraction diagram containing at least the principal characteristic peaks of at least one of alpha, rho, khi, eta, gamma, kappa, theta and delta transition aluminas, and recovering an effluent from the oligomerization.

2. A process according to claim 1, in which the catalyst has a pore distribution such that:
    the ratio between the volume V2, measured by mercury porosimetry, in the range between $D_{mean}$–30 Å and $D_{mean}$+30 Å, to the total mercury volume is more than 0.6;
    the volume V3, measured by mercury porosimetry, in pores with diameters of more than $D_{mean}$+30 Å, is less than 0.1 ml/g; and
    the volume V6, measured by mercury porosimetry, in pores with diameters of more than $D_{mean}$+15 Å, is less than 0.2 ml/g.

3. A process according to claim 1, in which the X ray diffraction diagram of the catalyst contains at least the principal characteristic peaks of at least one of eta, theta, delta and gamma transition aluminas.

4. A process according to claim 1, in which the X ray diffraction diagram of the catalyst contains at least the principal characteristic peaks of at least one of eta and gamma transition aluminas.

5. A process according to claim 1, said catalyst containing a cationic impurities content in the catalyst support of less than 0.1% by weight.

6. A process according to claim 1, said catalyst containing an anionic impurities content in the catalyst support of less than 0.5% by weight.

7. A process according to claim 1, in which the catalyst support comprises at least two silica-alumina zones having Si/Al ratios which are higher or lower than the overall Si/Al ratio determined by X ray fluorescence.

8. A process according to claim 1, in which the catalyst support comprises a single silica-alumina zone having a Si/Al ratio equal to the overall Si/Al ratio determined by X ray fluorescence and less than 2.3.

9. A process according to claim 1, in which the catalyst comprises at least one metallic element selected from the group consisting of elements from groups IVB, VB and VIB and from the first series of group VIII of the periodic table.

10. A process according to claim 1, in which the catalyst comprises silicon as a doping element deposited on the support.

11. A process according to claim 1, in which the olefins derive from one or more sources selected from catalytic cracking units, steam cracking units, paraffin dehydrogenation units, units for polymerizing dehydration of methanol to water and light olefins, and any other source of light olefins.

12. A process according to claim 1, in which the olefinic cut sent to the oligomerization catalyst is free of impurities such as water, sulfur-containing derivatives or basic nitrogen-containing derivatives before being introduced into the oligomerization reactor.

13. A process according to claim 1, comprising the following steps:
    oligomerizing an olefinic C4 cut, limiting the overall conversion of n-butenes to less than 10% while more than 90% of the quantity of isobutene is converted into dimers and trimers; and
    distilling the oligomerization effluent to obtain a fraction (a light effluent) which contains more than 90% by weight of butane, isobutane and butenes which have not reacted during the oligomerization, at least a portion of said fraction then supplying an alkylation unit or a hydration unit, and another fraction constituted by the oligomers obtained subsequently used as a gasoline base.

14. A process according to claim 13, in which the oligomerization reaction is carried out at a temperature between 30° C. and 300° C., at a pressure in the range 0.1 to 20 MPa and with a volume of hydrocarbon feed per volume of catalyst per hour in the range 0.05 to 5 $h^{-1}$.

15. A process according to claim 13, in which the oligomers obtained are re-injected into a supplementary oligomerization reactor.

16. A process according to claim 13, in which the light effluent is introduced into a hydroisomerization reactor.

17. A process according to claim 1, in which an olefinic C4 cut or an olefinic C3-C4 cut undergoes oligomerization such that less than 80% of the butenes contained in the feed are converted and at least 80% of the isobutene contained in the feed is converted into dimers or trimers.

18. A process according to claim 17, in which the oligomerization reaction is carried out at a temperature between 40° C. and 250° C., a pressure between 0.1 and 10 MPa and with a volume of hydrocarbon feed per volume of catalyst per hour between 0.05 and 5 $h^{-1}$.

19. A process according to claim 17, in which the olefinic feed is substantially free of isobutene.

20. A process according to claim 1, comprising the following steps:
    a first oligomerization step, in which an olefinic C4 or C3-C4 cut is treated in a first oligomerization reactor in which the overall conversion of n-butenes contained in the feed is less than 45% and the isobutene conversion is more than 80%, the oligomers obtained being more than 80% dimers and trimers;
    the effluent from the first oligomerization step is sent to a fractionation column to recover a first fraction containing isobutene and unconverted n-butenes and a second fraction consisting of 90% dimers and trimers from the oligomerization reaction;
    a second oligomerization step, in which the first recovered fraction is introduced into a second oligomerization reactor in which at least 50% of the n-butenes are converted; and
    the effluent from the second oligomerization step is sent to the fractionation column associated with the first oligomerization reactor or to a second column.

21. A process according to claim 20, in which the oligomerization reactions are carried out at a temperature in the range 40° C. to 250° C., at a pressure in the range 0.1 to 10 MPa, and with a quantity of hydrocarbon feed per volume of catalyst per hour in the range 0.05 to 5 $h^{-1}$.

22. A process according to claim 1, in which an olefinic C4 cut or an olefinic C3-C4 cut undergoes oligomerization such that at least 90% of the 1-butene, at least 80% of the 2-butenes and at least 97% of the isobutene are converted.

23. A process according to claim 22, in which the oligomerization reaction is carried out at a temperature in the range 60° C. to 250° C., at a pressure in the range 0.1 to 10 MPa, and with a quantity of hydrocarbon feed per volume of catalyst per hour in the range 0.05 to 5 $h^{-1}$.

24. A process according to claim 1, in which an olefinic C3 cut undergoes oligomerization such that at least 80% of the propylene contained in the feed is converted.

25. A process according to claim 24, in which the oligomerization reaction is carried out at a temperature between 30° C. and 300° C., at a pressure in the range about 0.1 to 20 MPa, and with a volume of hydrocarbon feed per volume of catalyst per hour in the range 0.05 to 5 $h^{-1}$.

26. A process according to claim 1, in which the oligomerization is conducted in a fixed bed reactor.

27. A process according to claim 1, in which at least a portion of unconverted effluent is recycled to the oligomerization.

28. A process according to claim 1, in which the feed is diluted by adding aliphatic or cyclic paraffins deriving from another source, having the same molecular weight and/or being heavier than the olefinic feed.

29. A process according to claim 1, in which the effluent comprises an olefinic cut having an initial boiling point at a temperature of more than 150° C.

30. A process according to claim 29, in which the olefinic cut is subsequently partially or completely hydrogenated.

31. A process according to claim 1, in which the mean pore diameter of the catalyst, measured by mercury porosimetry, is in the range 40 to 120 Å.

32. A process according to claim 1, said catalyst having a pore volume measured by mercury porosimetry, included in pores with a diameter of more than 500 Å, of less than 0.05 ml/g.

33. A process according to claim 1, said catalyst having a pore volume measured by mercury porosimetry, included in pores with a diameter of more than 500 Å, of less than 0.02 ml/g.

34. A process according to claim 1, said catalyst having a pore volume measured by mercury porosimetry, included in pores with a diameter of more than 500 Å, of less than 0.01 ml/g.

* * * * *

UNITED STATES PATENT AND TRADEMARK OFFICE
CERTIFICATE OF CORRECTION

PATENT NO. : 7,572,946 B2
APPLICATION NO. : 11/182021
DATED : August 11, 2009
INVENTOR(S) : Lacombe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 999 days.

Signed and Sealed this

Fourteenth Day of December, 2010

David J. Kappos
*Director of the United States Patent and Trademark Office*